US006566539B1

(12) United States Patent
Campos et al.

(10) Patent No.: US 6,566,539 B1
(45) Date of Patent: May 20, 2003

(54) CATALYST REGENERATION BY TREATMENT WITH AN OXIDIZING AGENT

(75) Inventors: Daniel Campos, Lancaster, PA (US); Richard Edward Ernst, Kennett Square, PA (US); John Byrne Michel, West Chester, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/198,424

(22) Filed: Jul. 18, 2002

(51) Int. Cl.$^7$ ............... C07D 307/08; C07D 307/20; C07C 27/08
(52) U.S. Cl. ............ 549/326; 549/508; 568/864; 502/40; 502/41
(58) Field of Search ............... 549/326, 508; 568/864; 502/40, 41

(56) References Cited

U.S. PATENT DOCUMENTS

| 4,006,165 A | 2/1977 | Michalczyk et al. |
| 4,331,557 A | 5/1982 | Drake |
| 5,478,952 A | 12/1995 | Schwartz |
| 5,698,749 A | 12/1997 | Pedersen et al. |
| 6,008,384 A | 12/1999 | Bockrath et al. |
| 6,225,477 B1 | 5/2001 | Ernst et al. |

OTHER PUBLICATIONS

Junichi Kanetaka, Seiichi Kiryu, Taisuke Asano, Shinobu Masamyne, "Hydrogenation of Maleic Anhydride and Intermediates by Nickel–Rhenium Catalyst Supported on Kieselguhr", Bulletin of Japan Petroleum Institute, vol. 12, pp. 89 to 96 (1970).

*Primary Examiner*—Taofiq Solola

(57) ABSTRACT

A process for the production of tetrahydrofuran, gamma butyrolactone, 1,4-butane diol and the like from a hydrogenatable precursor such as maleic acid, succinic acid, corresponding esters and their mixtures and the like in the presence of hydrogen and a noble metal catalyst, wherein oxidizing agents such as hydrogen peroxide, oxygen or air are used to regenerate spent noble metal catalyst for further use in the process.

20 Claims, 5 Drawing Sheets

CATALYST REGENERATION BY TREATMENT WITH AN OXIDIZING AGENT

BACKGROUND OF THE INVENTION

1. Field of the Invention

This invention relates to a process for the production of tetrahydrofuran, gamma butyrolactone, 1,4-butane diol and the like from a hydrogenatable precursor such as maleic acid, succinic acid, corresponding esters and their mixtures and the like in the presence of hydrogen and a noble metal catalyst, and more specifically to a process for regenerating spent catalyst from the process.

2. Description of the Related Art

Various methods and reaction systems have been proposed in the past for manufacturing tetrahydrofuran (THF) and 1,4 butane diol (BDO) by catalytic hydrogenation of gamma butyrolactone, maleic acid, maleic anhydride, succinic acid or related hydrogenatable precursors. Also, a variety of hydrogenation catalysts have been historically proposed for this purpose including various transition metals and their combinations deposited on various inert supports, all as generally known in the art. Many of these catalysts are proposed for use in hydrogenations carried out in an organic solvent or organic reaction media and not in an aqueous solution phase. In fact, at least one prior publication suggests that water and succinic acid may be considered as inhibitors to the desired catalysis, see Bulletin of Japan Petroleum Institute, Volume 12, pages 89 to 96 (1970).

U.S. Pat. No. 5,698,749 discloses a process for producing 1,4-butanediol by aqueous hydrogenation of a hydrogenatable precursor using a catalyst comprised of a noble metal of Group VIII and at least one of rhenium, tungsten and molybdenum, on a carbon support pretreated with an oxidizing agent. The purpose of this pretreatment is to increase the yield of butanediol relative to gamma butyrolactone or tetrahydrofuran, as compared to the use of a catalyst made with un-pretreated carbon.

On extended use of noble metal catalysts, the reaction rate for the hydrogenation typically slows down to the point where the deactivated or spent catalyst must be replaced with fresh catalyst. The old catalyst may then be destroyed by burning off the carbon, followed by partial recovery of the expensive metal ingredients. The overall cost of catalyst replacement is quite high. Similar deactivation problems are typically found with other noble metal catalysts in this process. Typically, many factors may combine to cause such deactivation, and even finding these causes may not directly lead to a method for regenerating a deactivated catalyst. While the literature describes a number of methods for regeneration of noble metal hydrogenation catalysts, many of these have failed or been found inadequate in practice.

In processes for the production of tetrahydrofuran, gamma butyrolactone, 1,4-butane diol and the like from a hydrogenatable precursor in an aqueous solution in the presence of hydrogen and a noble metal catalyst, there is a need for a more economical method for the regeneration of the spent noble metal catalysts, or for extending the active life of such catalysts.

SUMMARY OF THE INVENTION,

This invention relates to a process for production of tetrahydrofuran, gamma butyrolactone, 1,4 butanediol and the like from a hydrogenatable precursor such as maleic acid, succinic acid, corresponding esters and their mixtures and the like in the presence of hydrogen using a noble metal catalyst, the improvement comprising the treatment of deactivated noble metal catalyst by contacting with from about 0.1% to about 20% of oxidizing agent relative to the dry weight of the catalyst and at a temperature ranging from ambient to about 300° C.

DETAILED DESCRIPTION OF THE INVENTION

Figure 1:
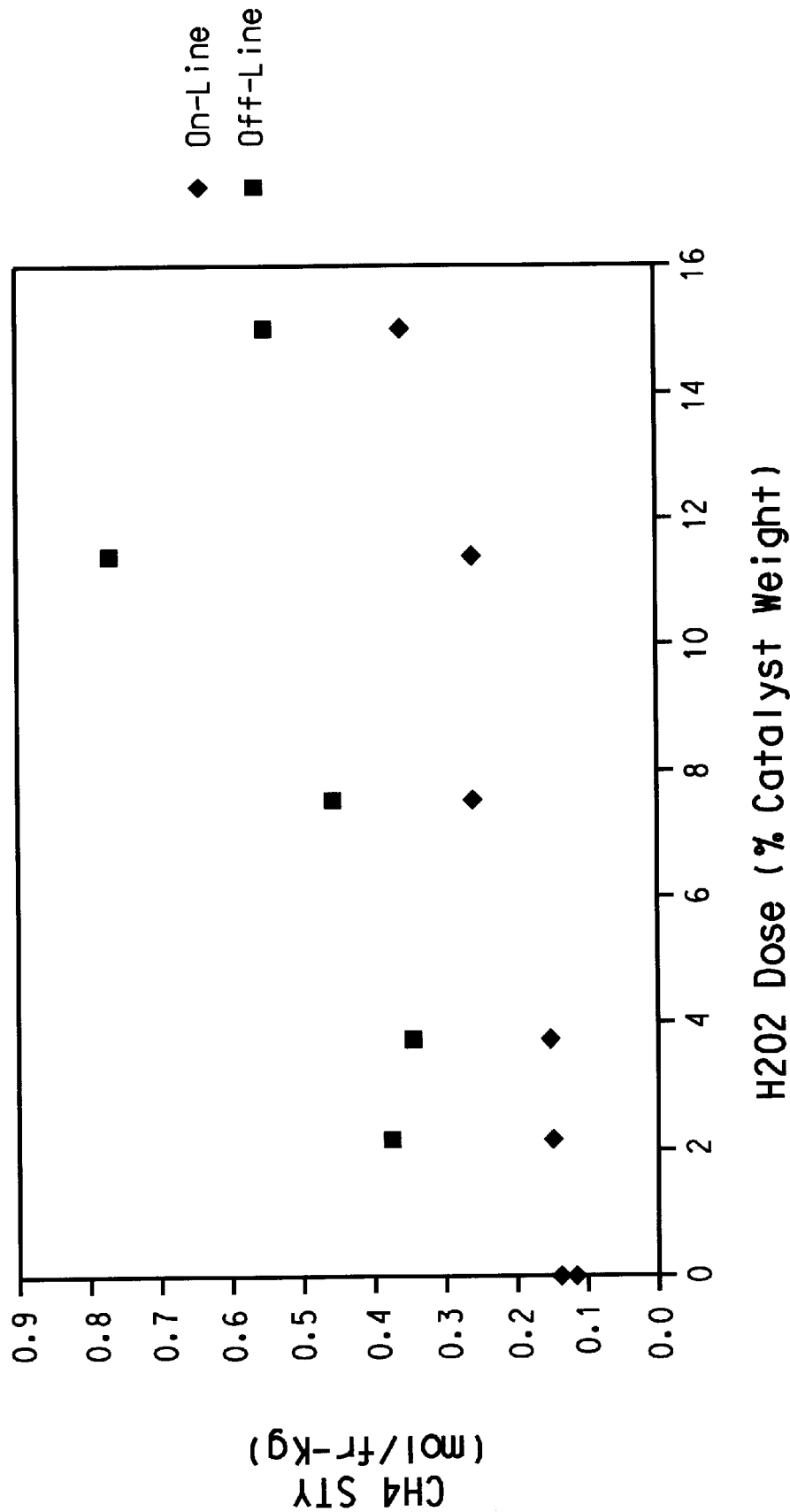
FIG. 1 is a graph showing the effect of $H_2O_2$ addition on catalyst methanation activity.
Figure 2:
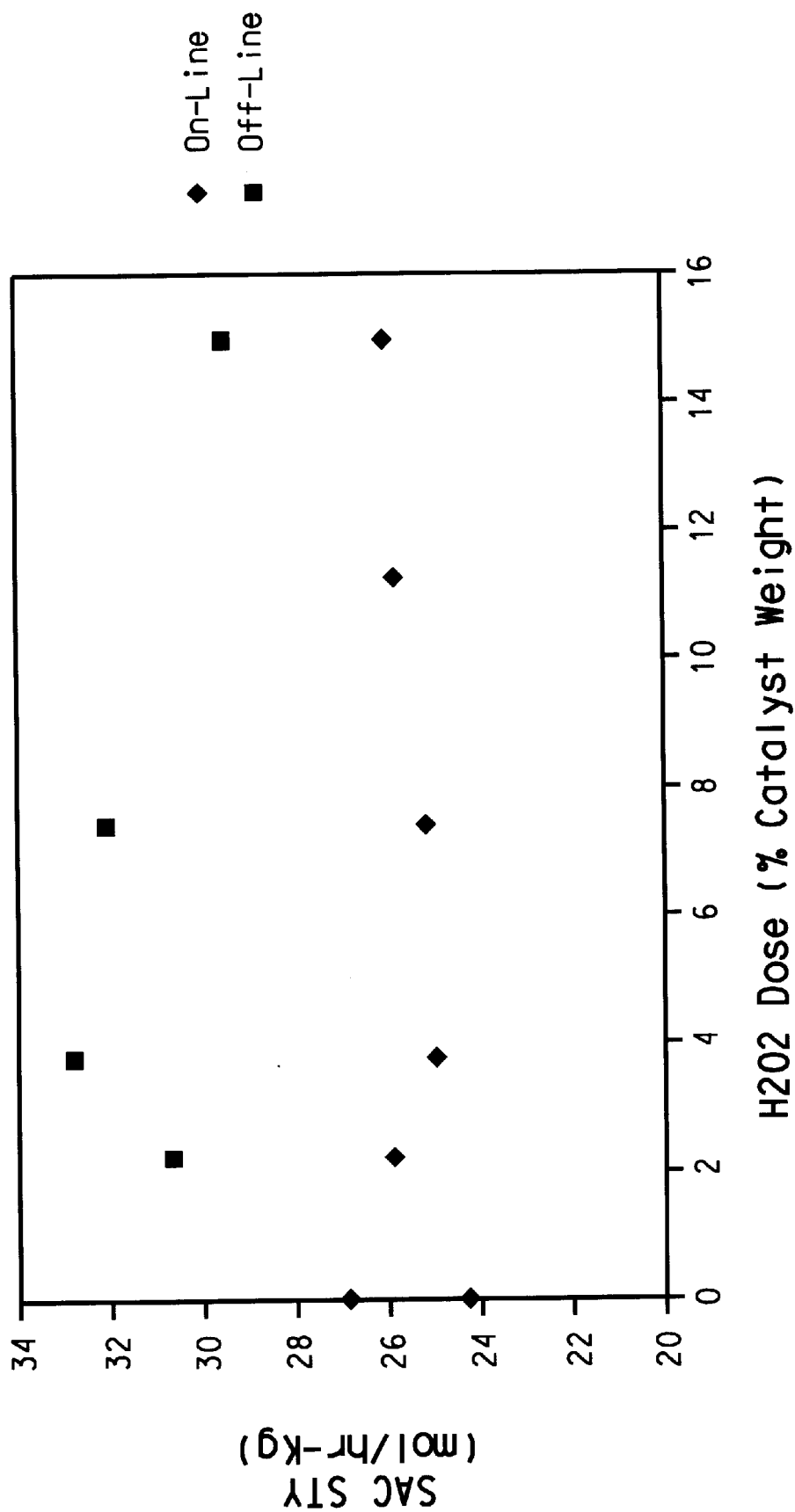
FIG. 2 is a graph showing the effect of $H_2O_2$ addition on catalyst activity to convert SAC.
Figure 3:
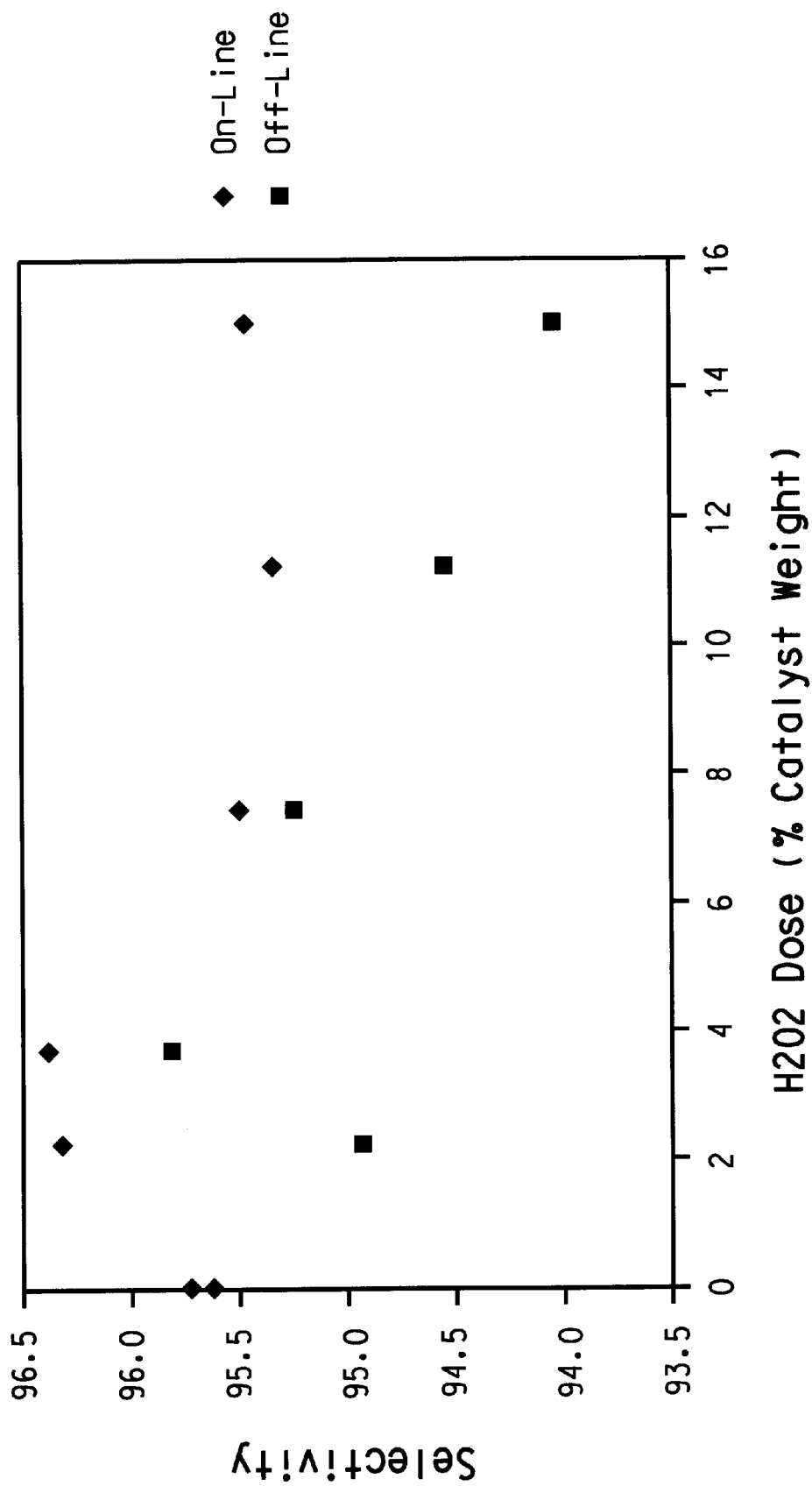
FIG. 3 is a graph showing the effect of $H_2O_2$ addition on catalyst selectivity to convert SAC to useful products.
Figure 4:
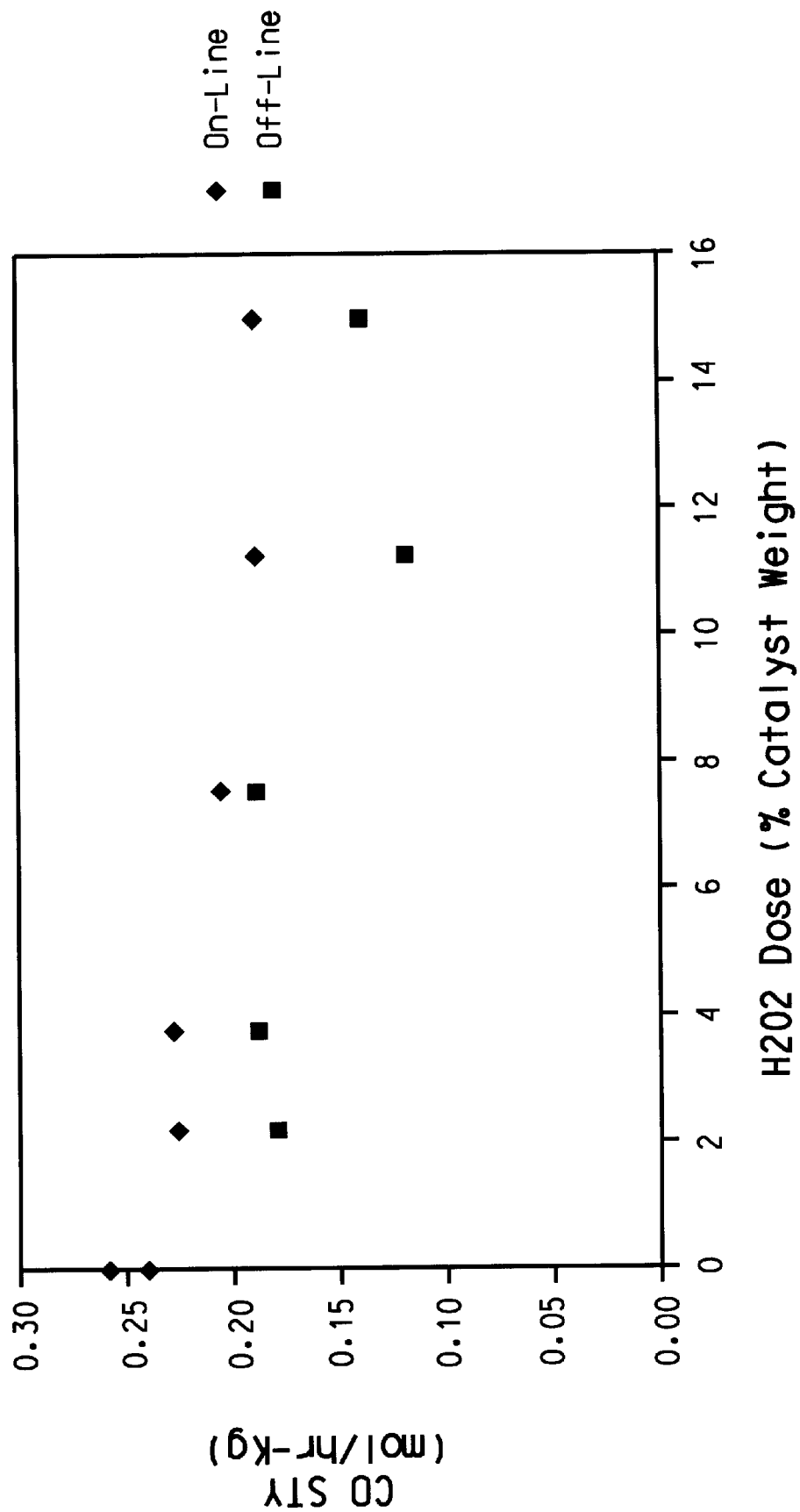
FIG. 4 is a graph showing the effect of $H_2O_2$ treatment on catalyst net CO production rate.

In the production of tetrahydrofuran (THF), gamma butyrolactone (GBL) and 1,4 butanediol (BDO) by aqueous hydrogenation of maleic acid (MAC) and succinic acid (SAC), various noble metal catalysts are employed. For example, U.S. Pat. No. 5,478,952 and 6,008,384 disclose the use of specific ruthenium-rhenium and ruthenium-rhenium-tin catalysts in this process. As is typical for noble metal hydrogenation catalysts, the activities of these catalysts decline steadily with their use in production. They can lose a substantial part of their initial activity in a period as short as several months.

We have also found that one of the causes for this decrease in activity as well as a decrease in selectivity is the presence of carbon monoxide (CO), a known poison of transition-metal catalysts. It is believed that the CO is formed by decarbonylation and decarboxylation of reactants and intermediates during the hydrogenation reaction. Since excess hydrogen is recycled, the CO concentration in the recycled hydrogen tends to build up until it reaches a level in equilibrium with the losses from the hydrogen purge stream. The CO level may rise to 3000 ppm depending on time and the acid level in the reactants. Laboratory tests show that a CO level between 2000 to 3000 ppm depresses catalyst activity quite significantly. While a fresh catalyst may protect itself from CO poisoning by efficiently converting CO to innocuous $CH_4$ (methanation), within the first month of operation, a catalyst can lose more than half of its ability to convert CO to $CH_4$.

In the inventive process, a deactivated noble metal catalyst is contacted with an oxidizing agent to restore a major part of its previous activity. The oxidizing agent is preferably $H_2O_2$, oxygen or air. The amount of oxidizing agent used is from about 0.1% to about 20% (100% oxidant basis) relative to the dry weight of the catalyst. The term 100% oxidant basis refers to the amount of oxidizing agent needed based on purity. For example, $H_2O_2$ is not generally available at 100% purity and 35% $H_2O_2$ is typically used. Therefore, 35 Kg of $H_2O_2$ on 100% basis requires 100 Kg of 35% $H_2O_2$. Below 0.1%, the benefit is not significant. Above 20%, the catalyst activity and selectivity may be adversely affected. Preferably, the amount of oxidizing agent used is from about 0.5 to about 10% by weight of the catalyst. More preferably it is from about 1% to about 5% by weight of the catalyst.

The contacting step may be carried out with the catalyst under a wide variety of conditions. The catalyst may be treated in a dried or slurry form. It may be treated as a separate operation (off-line) or as part of the hydrogenation process (on-line). The treatment may be carried out in the hydrogenation reaction equipment (in-situ) or in separate equipment (ex-situ). If the treatment is on-line, it is typically conducted in situ.

The catalyst may be contacted with the oxidizing agent at a temperature ranging from ambient temperature (about 20° C.) to about 300° C., preferably from ambient temperature to about 250° C. When the treatment is carried out off-line, contacting is conveniently done at temperatures from ambient up to reflux temperature, which typically depends on the boiling point of the solvent. When the treatment is carried out on-line, it may be done at the operating temperature of the hydrogenation process (about 150° C. to about 300° C.). The resulting regenerated catalyst has nearly the same activity as new catalyst. Moreover, because the regenerated catalyst has already been conditioned by the initial use, it may not take as long to "break in" as a new catalyst and, as such, its selectivity is higher from the outset than that of new catalyst.

It is believed that the mechanism for catalyst deactivation is consistent with the catalyst sites being fouled by high-boiler organics which can accumulate over time in a long-term run. Therefore, it is quite surprising that the addition of an oxidizing agent to the catalyst improves catalyst activity, because during the oxidizing treatment nothing is physically removed from the catalyst slurry. While not being held to any theory, it may be that the oxidizing agent partially oxidizes the organic foulants, which are strongly adsorbed on the catalyst, and the oxidized foulants then desorb from the catalyst surface, freeing catalyst sites. This then would lead to the observed catalyst activity increase.

It is even more surprising that this oxidation can also be performed on-line under hydrogen reduction conditions, because reduction conditions are typically incompatible with an oxidation reaction.

This process may be applied periodically in the reactor (on-line) or during scheduled shutdowns (off-line). The time between treatments would depend on the catalyst deactivation rate. The process may be carried out in the reaction equipment or in separate facilities. Typically, separate facilities are used only for off-line processes. It may be used in a slurry, fixed bed or fluidized bed hydrogenation system.

Although off-line treatment is typically more effective than on-line treatment, the latter has the advantage that it can be implemented without a process shutdown. As shown in Example 1, the required on-line $H_2O_2$ dose for a deactivated catalyst such as the 249-day sample is at least 5% $H_2O_2$. Optionally, such a dose could be introduced over a 30-day period, which would require a continuous addition rate of about 0.17%/day.

During such on-line treatment, in certain systems the oxidizing agent may preferentially attack MAC or useful intermediates, instead of the high-boilers. This would become apparent in reduced yields that would have to be weighed against the benefit of increased catalyst activity.

Also, during the oxidation treatment with $H_2O_2$, free oxygen may be released. During hydrogenation, the oxygen content of the hydrogen should be carefully monitored to make sure that it is well outside the range for combustible (i.e., explosive) conditions. This should not be a problem if the recommended feed rates are followed. This is preferably accomplished by limiting the feed rate of the oxidizing agent. The same precautions apply to an even greater extent if air or oxygen is used as the oxidizing agent.

If the oxidation treatment is carried out prior to the addition of hydrogen to the system, any oxygen should either be removed from the system before the addition of hydrogen, or the temperature of treatment should be raised to the point where water vapor effectively reduces the partial pressure of the oxygen so that there is no crossover into combustible conditions during hydrogen pressurization.

The following describes a process for applying $H_2O_2$ treatment off-line and in-situ to a slurry catalyst system:

(1) Stop the organics feed and all recycle streams (MAC, BDO, GBL, etc.) to hydrogenator and hydrogenate the slurry until system acidity is reduced to zero. Add water as needed to maintain a constant level.

(2) Reduce the reactor temperature to about 50° C. or lower if practical.

(3) Reduce reactor pressure to about 1000 psi or lower (i.e., to a pressure level that the compressor can maintain after switching from $H_2$ to nitrogen).

(4) Replace the $H_2$ feed with nitrogen fed at a sufficient rate to maintain slurry agitation, and purge all $H_2$.

(5) Gradually feed a weight (100% basis) of $H_2O_2$ equal to about 4% of the dry catalyst weight in the reactor while monitoring the $O_2$ concentration in the gas recycle loop.

(6) Gradually, increase the reactor temperature to about 190° C. while recycling the gas with little or no purge to retain the $O_2$ in the system. During this step the $O_2$ concentration should decrease gradually as the organics on the catalyst are oxidized.

(7) When 190° C. is reached, purge the residual $O_2$ with nitrogen.

(8) When the $O_2$ concentration in the recycle loop is negligible, switch the nitrogen feed to $H_2$ and purge all nitrogen and other inert gases.

(9) Increase reactor pressure to standard operating level and resume the organics feed.

A similar process may be used for applying $H_2O_2$ treatment off-line and in-situ to a fixed bed or fluidized bed catalyst system catalyst system. The following describes a typical treatment procedure for such systems, which may be readily modified by one skilled in the art to fit a particular reaction system:

(1) Stop the feed of all organic compounds to the hydrogenator.

(2) Reduce the reactor temperature to about 50° C. or lower.

(3) Reduce reactor pressure to about 1000 psi or lower.

(4) Replace the $H_2$ feed with nitrogen and purge all $H_2$.

(5) Gradually feed a weight of $H_2O_2$ equal to about 4% of the dry catalyst weight in the reactor while monitoring the $O_2$ concentration in the gas recycle loop.

(6) Gradually increase the reactor temperature to standard hydrogenation temperature while recycling the gas with little or no purge to retain the $O_2$ in the system.

(7) When the standard hydrogenation temperature is reached, purge the residual $O_2$ with nitrogen.

(8) When the $O_2$ concentration in the recycle loop is negligible, switch nitrogen feed to $H_2$ and purge all nitrogen and other inert gases.

(9) Increase reactor pressure to standard operating level and resume organics feed.

The process may also be applied on-line (i.e., during normal operation) to either a slurry catalyst system, fixedbed catalyst system or fluidized bed catalyst system by continuously feeding small amounts of $H_2O_2$ or air in the reactor along with the reagents feed. The recommended rate of addition of $H_2O_2$ or $O_2$ is between 0.01 to 0.5% /day (100% basis) relative to the total catalyst weight (which includes the weight of the support).

A preferred continuous regeneration procedure in such a system is described in the section below:

(1) While continuing hydrogen and organic reagents feeds to the reactor, pump $H_2O_2$ aqueous solution continuously at a rate such that the feed of $H_2O_2$ is between 0.01 to 0.5% of the weight of the catalyst per day. The $H_2O_2$ can be premixed with the organic reagents and co-fed in this manner to the reactor, or can be fed separately.

(2) Monitor the free $O_2$ content in the $H_2$ off-gas to insure that it is outside the explosive limits. If necessary, adjust the feed rate of $H_2O_2$ to insure this.

(3) When the desired degree of regeneration has been achieved, discontinue the feed of $H_2O_2$ and resume regular operation.

It is to be recognized that many variations in the specific regeneration procedure used will be apparent to one skilled in the art, and all such procedures are included within the scope of the present invention.

The regeneration process is applicable to any noble metal catalyst used for the production of tetrahydrofuran, gamma butyrolactone, and 1,4 butanediol by aqueous hydrogenation of maleic acid and succinic acid. These noble metal catalysts include those containing, for example, ruthenium, rhenium, platinum, and palladium. Other metals, such as tin, molybdenum, or silver may be present to aid in or modify the reaction. The noble metal catalysts and the other metals will typically be located on a support such as carbon, alumina, silica or other support materials known in the art. Preferably, a carbon support is used.

EXAMPLES

The following examples were carried out on catalyst samples removed from a continuous reactor producing THF by the aqueous hydrogenation process previously described and then subjected to a standard autoclave batch test as described:

The standard autoclave batch test consists of charging the reactor with 0.4 g on dry basis of catalyst with 125 g of 7% succinic acid (SAC) solution. Then the mixture is heated to about 250° C. while stirring at 700 RPM. When the target temperature is reached, $H_2$ is added to the reactor to give a pressure of 2000 Psi. The pressure is held constant by continuous feed of the $H_2$ for 45 min while the mixture is stirred at 700 RPM. After 45 min, the reactor is immediately cooled to room temperature. Liquid and gas samples are taken and analyzed by gas chromatograph. The space-time yield (STY) for a given species is determined as the difference between the final and initial moles of said species per unit time per unit mass of catalyst on dry basis. The selectivity is determined as the ratio of the moles of THF+BDO+GBL produced to the total moles of products and byproducts produced at the end of the test.

Examples 1–7 and Comparative Examples

These examples were done with the oxidation treatment carried out in the absence of hydrogen. A used slurry catalyst consisting of 2% Ru, 6% Re, 0.9% Sn on carbon that had run in a continuous reactor for 249 days was tested in accordance with the standard batch-test as described above and as follows:

Comparative Examples A–B

A precise weight of the well-mixed slurry was taken to give 0.4 g of catalyst on dry basis for the standard autoclave batch test. No oxidizing treatment was done.

Examples 1–7

The procedure was the same as for the comparative examples above, except that the slurry was loaded in the reactor and mixed with a given amount of $H_2O_2$ (using 3% $H_2O_2$ aqueous solution). Several tests were run in this manner with the $H_2O_2$ dose varied between 2.25 and 45% (100% basis) relative to the catalyst weight. The $H_2O_2$ was added to the test solution (7% SAC) containing the catalyst at room temperature. The $H_2O_2$ began to react with the catalyst almost instantly. Then the reactor was closed and heated in the absence of $H_2$ to operating temperature, which took about 40 minutes. Then $H_2$ was added to the reactor and the test begun.

TABLE 1

Off-Line Treatment

| Example | $H_2O_2$ dose (% of catalyst weight) | $CH_4$ STY mol/hr-Kg | CO STY (mol/hr-Kg) | $CO_2$ STY* mol/hr-Kg | SAC STY mol/hr-Kg | Selectivity |
|---|---|---|---|---|---|---|
| A | 0.00 | 0.119 | 0.238 | 0.374 | 24.24 | 95.6 |
| B | 0.00 | 0.137 | 0.257 | 0.411 | 26.79 | 95.8 |
| 1 | 2.25 | 0.375 | 0.178 | 0.464 | 30.69 | 94.9 |
| 2 | 3.75 | 0.343 | 0.188 | 0.480 | 32.83 | 95.8 |
| 3 | 7.50 | 0.459 | 0.187 | 0.476 | 32.04 | 95.2 |
| 4 | 11.25 | 0.773 | 0.120 | 0.584 | 34.81 | 94.5 |
| 5 | 15.00 | 0.546 | 0.137 | 0.512 | 29.43 | 94.0 |
| 6 | 22.50 | 0.599 | 0.137 | 0.582 | 25.14 | 93.9 |
| 7 | 45.00 | 0.596 | 0.085 | 0.988 | 20.57 | 92.0 |

Examples 8–12 and Comparative Examples

These examples are with the oxidation treatment carried out in the presence of hydrogen. A used slurry catalyst consisting of 2% Ru, 6% Re, 0.9% Sn on carbon that was run in a continuous reactor for 249 days was tested in the batch reactor by the standard batch-test and as follows:

Comparative Examples C–D

A precise weight of the well-mixed slurry is precisely weighed to give 0.4 g of catalyst on dry basis for the standard autoclave batch test. No oxidizing treatment was done Examples 8–12

The procedure was the same as for the comparative examples above, except that a given $H_2O_2$ dose was added to the reactor simultaneously with $H_2$ at 250° C.

TABLE 2

On-Line Treatment

| Example | $H_2O_2$ dose (% of catalyst weight) | $CH_4$ STY mol/hr-Kg | CO STY (mol/hr-Kg) | $CO_2$ STY* mol/hr-Kg | SAC STY mol/hr-Kg | Selectivity |
|---|---|---|---|---|---|---|
| C | 0.00 | 0.119 | 0.238 | 0.374 | 24.24 | 95.6 |
| D | 0.00 | 0.137 | 0.257 | 0.411 | 26.79 | 95.8 |

TABLE 2-continued

On-Line Treatment

| Example | $H_2O_2$ dose (% of catalyst weight) | $CH_4$ STY mol/hr-Kg | CO STY (mol/hr-Kg) | $CO_2$ STY* mol/hr-Kg | SAC STY mol/hr-Kg | Selectivity |
|---|---|---|---|---|---|---|
| 8  | 2.25  | 0.154 | 0.223 | 0.583 | 25.93 | 96.3 |
| 9  | 3.75  | 0.154 | 0.223 | 0.755 | 24.96 | 96.4 |
| 10 | 7.50  | 0.255 | 0.204 | 1.634 | 25.06 | 95.5 |
| 11 | 11.25 | 0.254 | 0.187 | 2.306 | 25.75 | 95.3 |
| 12 | 15.00 | 0.358 | 0.188 | 3.549 | 25.97 | 95.5 |

Figure 5:
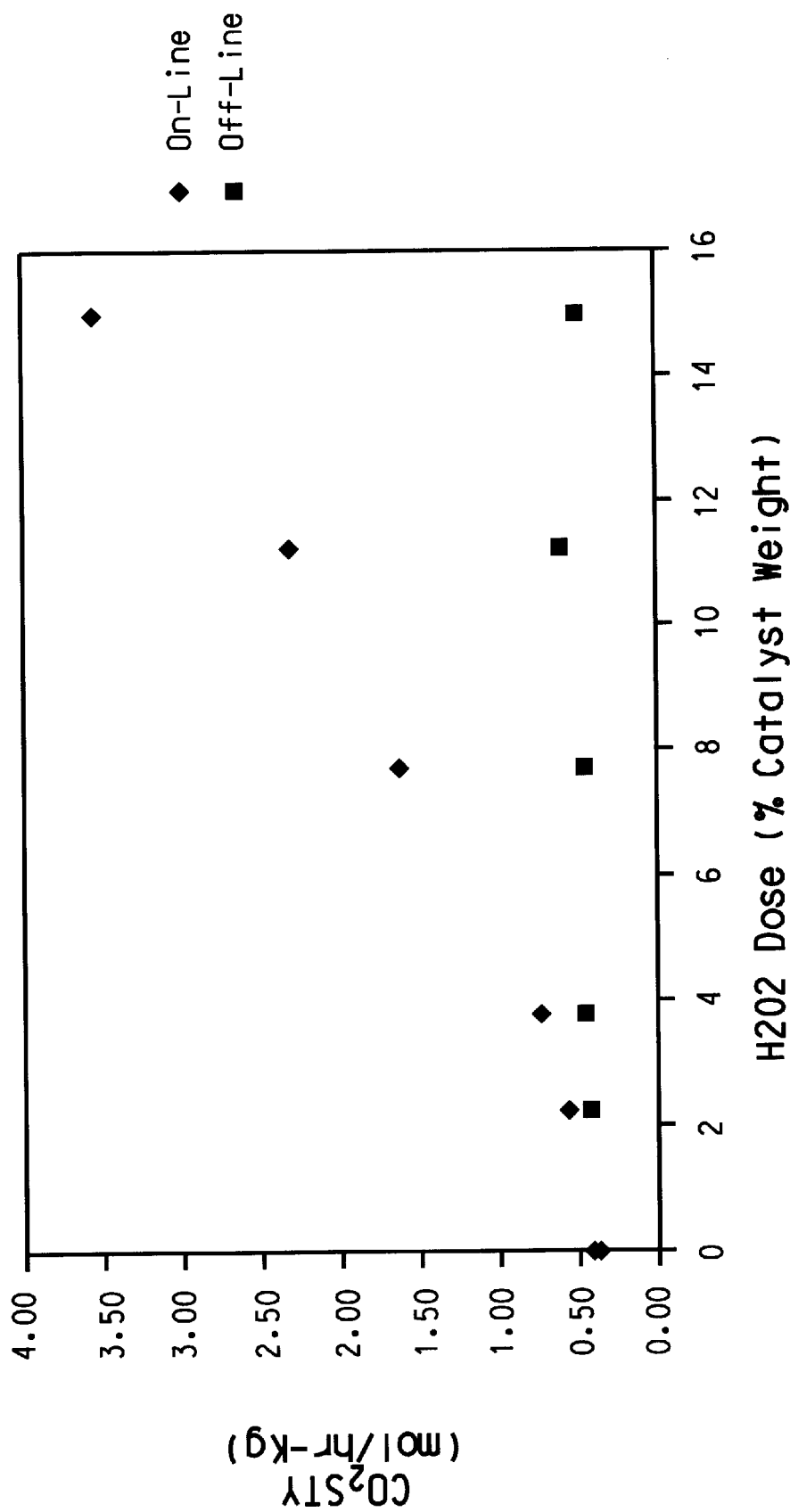
FIG. 5 is a graph showing the effect of $H_2O_2$ treatment on $CO_2$ production rate.

The data from Tables 1 and 2, together with FIGS. 1 to 5, show the effect of using various amounts of oxidant, and compare the results of off-line (no hydrogen) and on-line (with hydrogen) treatment conditions. It is noted that catalyst activity to produce C)$_2$ is increased by on-line $H_2O_2$ addition as depicted in FIG. 5. This effect is much stronger when $H_2O_2$ is added on-line than when added off-line and it is believed that some of the $CO_2$ results from the oxidation of catalyst foulants.

Examples 13–16 and Comparative Examples

A used slurry catalyst consisting of 2% Ru, 6% Re, 0.9% Sn on carbon that was run in a continuous reactor for 202 days was tested in the batch reactor by a standard batch-test and as follows:

Comparative Examples E–H

A precise weight of the well-mixed slurry was taken to give 0.4 g of catalyst on dry basis for the standard autoclave batch test. No oxidizing treatment was done.

Examples 13–16

Same as above, except that the slurry was loaded in the reactor and pressurized with enough air to provide 0.2 g oxygen per g of catalyst (20% of the catalyst weight). Here the mixing of air and catalyst occurred in the absence of $H_2$ for about 40 minutes until the operating temperature of 250° C. was reached.

TABLE 3

Off-Line Air Treatment

| Example | Catalyst treatment | $CH_4$ STY mol/hr-Kg | CO STY (mol/hr-Kg) | $CO_2$ STY* mol/hr-Kg | SAC STY mol/hr-Kg | Selectivity |
|---|---|---|---|---|---|---|
| E  | none       | 0.189 | 0.207 | 0.413 | 27.39 | 94.6 |
| F  | none       | 0.134 | 0.201 | 0.369 | 28.63 | 94.3 |
| G  | none       | 0.189 | 0.206 | 0.446 | 28.44 | 94.9 |
| H  | none       | 0.138 | 0.224 | 0.379 | 26.82 | 94.9 |
| 13 | air-treated | 0.414 | 0.172 | 0.759 | 30.40 | 93.0 |
| 14 | air-treated | 0.364 | 0.173 | 0.798 | 29.23 | 93.5 |
| 15 | air-treated | 0.347 | 0.173 | 0.797 | 28.75 | 93.5 |
| 16 | air-treated | 0.348 | 0.174 | 0.661 | 29.40 | 93.7 |

The data in Table 3 show that air treatment significantly increases the methanation activity and favorably reduces the CO production rate.

Although, the effect on the SAC activity is not apparent in the batch test, in a continuous reactor with hydrogen recycle the SAC activity would be significantly improved with the treated catalyst because the CO concentration would be lower due to the increased methanation activity.

What is claimed is:

1. In a process for production of tetrahydrofuran, gamma butyrolactone, or 1,4 butanediol from a hydrogenatable precursor such as maleic acid, succinic acid, corresponding esters and their mixtures and the like in the presence of hydrogen using a noble metal catalyst, the improvement comprising, treating a deactivated noble metal catalyst by contacting with from about 0.1% to about 20% of an oxidizing agent relative to the dry weight of the catalyst at a temperature ranging from about 20° C. to about 300° C.

2. The process of claim 1, wherein the catalyst contains at least one noble metal selected from the group consisting of ruthenium; rhenium, platinum and palladium.

3. The process of claim 2, wherein the catalyst additionally contains a metal selected from the group consisting of tin, molybdenum and silver.

4. The process of claim 3, wherein the catalyst additionally contains tin.

5. The process of claim 1, wherein the catalyst is on a support comprising a material selected from the group consisting of carbon, alumina and silica.

6. The process of claim 5, wherein the catalyst is on a support comprising carbon.

7. The process of claim 1, wherein the oxidizing agent is selected from the group consisting of hydrogen peroxide, air and oxygen.

8. The process of claim 7, wherein the oxidizing agent is hydrogen peroxide.

9. The process of claim 7, wherein the oxidizing agent is air.

10. The process of claim 7, wherein from about 0.5% to about 10% of the oxidizing agent relative to the dry weight of the catalyst is used.

11. The process of claim 8, wherein from about 1% to about 5% of hydrogen peroxide relative to the dry weight of the catalyst is used.

12. The process of claim 1, wherein the hydrogenation process is carried out in a slurry reaction system.

13. The process of claim 1, wherein the hydrogenation process is carried out in a fixed bed reaction system.

14. The process of claim 1, wherein the hydrogenation process is carried out in a fluidized bed reaction system.

15. The process of claim 12, wherein the treatment is carried out with the hydrogenation shut down and by the following steps:
a) stopping the feed of all organic compounds to the hydrogenator,
b) hydrogenating the slurry until system acidity is reduced to zero,
c) adding water as needed to maintain a constant level,
d) reducing the reactor temperature to about 50° C. or lower,
e) reducing reactor pressure to about 1000 psi or lower,
f) replacing the hydrogen feed with nitrogen at a sufficient rate to maintain slurry agitation and purge all hydrogen,
g) gradually feeding a weight of $H_2O_2$ equal to about 4% of the dry catalyst weight in the reactor while monitoring the oxygen concentration in the gas recycle loop,
h) gradually increasing the reactor temperature to 190° C. while recycling the gas with little or no purge to retain the oxygen in the system,
i) purging the residual oxygen with nitrogen when 190° C. is reached,
j) switching nitrogen feed to hydrogen and purge all nitrogen and other inert gases when the oxygen concentration in the recycle loop is negligible, k) increasing reactor pressure to standard operating level, and l) resuming the feed of organics.

16. The process of either one of claims 12, 13 or 14, wherein the treatment is carried out in a hydrogenation system with the hydrogenation in progress by adding relatively small amounts of oxidizing agents over a period of time along with the reagents.

17. The process of claim 16, wherein the rate of oxidizing agent addition is between about 0.01 and 0.5% per day for sufficient period of time to achieve an amount of oxidizing agent of about 0.1% to about 20% relative to the total catalyst weight.

18. The process of claim 17, wherein the oxidizing agent is hydrogen peroxide.

19. The process of either of claims 13 or 14, wherein the treatment is carried out with the hydrogenation shut down and by the following steps:

a) stopping the feed of all organic compounds to the hydrogenator, b) reducing the reactor temperature to about 50° C. or lower, c) reducing reactor pressure to about 1000 psi or lower, d) replacing the hydrogen feed with nitrogen and purge all hydrogen, e) gradually feeding a weight of $H_2O_2$ equal to about 4% of the dry catalyst weight in the reactor while monitoring the oxygen concentration in the gas recycle loop, f) gradually increasing the reactor temperature to standard hydrogenation temperature while recycling the gas with little or no purge to retain the oxygen in the system, g) purging the residual oxygen with nitrogen when the standard hydrogenation temperature is reached, h) switching nitrogen feed to hydrogen and purging all nitrogen and other inert gases when the oxygen concentration in the recycle loop is negligible, i) increasing reactor pressure to standard operating level, and j) resuming the feed of organics.

20. A regenerated catalyst comprising at least one noble metal, wherein the regenerated catalyst has activity equal to and selectivity greater than a new catalyst comprising at least one noble metal.

* * * * *